United States Patent [19]
Greco

[11] 3,935,283
[45] Jan. 27, 1976

[54] PRODUCTION OF HYDROQUINONE
[75] Inventor: Nicholas P. Greco, Edgewood, Pa.
[73] Assignee: Koppers Company, Inc., Pittsburgh, Pa.
[22] Filed: Jan. 17, 1975
[21] Appl. No.: 542,086

Related U.S. Application Data
[63] Continuation-in-part of Ser. No. 267,534, June 29, 1972, Pat. No. 3,862,247, which is a continuation-in-part of Ser. No. 16,545, March 4, 1970, abandoned, and a continuation-in-part of Ser. No. 447,848, March 4, 1974, abandoned, which is a continuation-in-part of Ser. No. 296,260, Oct. 10, 1972.

[52] U.S. Cl.......... 260/621 M; 260/621 H; 260/625
[51] Int. Cl.$^2$.......................................... C07C 39/10
[58] Field of Search......... 260/621 M, 574, 575, 16, 260/545, 447, 848, 296, 260, 267, 534, 621 H, 625, 621 R

[56] References Cited
UNITED STATES PATENTS

| | | | |
|---|---|---|---|
| 2,198,249 | 10/1956 | Henke................................ | 260/509 |
| 2,665,313 | 1/1954 | Lisk.................................... | 260/621 |
| 3,383,416 | 5/1968 | Benner................................ | 260/575 |
| 3,862,247 | 1/1975 | Greco................................. | 260/621 |

*Primary Examiner*—James O. Thomas, Jr.
*Assistant Examiner*—W. B. Lone
*Attorney, Agent, or Firm*—Oscar B. Brumback; Herbert J. Zeh, Jr.

[57] ABSTRACT

Hydroquinone is made by contacting nitrobenzene in an aqueous acid medium with hydrogen at elevated temperatures and pressures in the presence of an acid resistant reducing catalyst until hydrogen absorption ceases, removing any unreduced nitrobenzene from the reaction medium, removing the catalyst from the reaction medium, thereafter maintaining the reaction medium containing the hydrogen reduction product at a temperature of 200° to 300°C. for a sufficient time to hydrolyze the reduction product to hydroquinone, and extracting the hydroquinone from the aqueous reaction medium.

7 Claims, No Drawings

PRODUCTION OF HYDROQUINONE

CROSS REFERENCE TO RELATED APPLICATIONS

In some aspects, this application is a continuation-in-part of my copending application Ser. No. 267,534, filed June 29, 1972 now U.S. Pat. No. 3,862,247 which, in turn, is a continuation-in-part of application Ser. No. 16,545, filed Mar. 4, 1970 now abandoned. In other aspects, this application is a continuation-in-part of my copending application Ser. No. 447,848, filed Mar. 4, 1974 now abandoned as a continuation of application Ser. No. 296,260, filed Oct. 10, 1972.

BACKGROUND OF THE INVENTION

This invention relates to a process for the production of hydroquinone by the hydrogenation of nitrobenzene to an amino product and the hydrolysis of the amino product to hydroquinone.

Hydroquinone is a widely used organic reducing agent. It has the characteristic of being easily oxidized to quinone and the quinone-like products. The principal large scale used of hydroquinone is as a photographic developer. Hydroquinone also inhibits the autoxidation of various materials and is used as an antioxidant for substances such as fats, oils, whole milk powders, vitamins, and the like.

Hydroquinone has been produced heretofore commercially by the oxidation of aniline in sulfuric acid with manganese dioxide or sodium dichromate to quinone and the reduction of the quinone with iron dust in water to hydroquinone. Other suggested methods of production have included the hydrolysis of p-halogenated phenols with aqueous alkali metal hydroxide solutions and the electrolytic oxidation of benzene to quinone in sulfuric acid and the later reduction of the quinone to hydroquinone. My copending application Ser. No. 267,534 describes the productioon of hydroquinone by the hydrolysis of para-aminophenol.

SUMMARY OF THE INVENTION

According to this invention hydroquinone is made from nitrobenzene by hydrogenating the nitrobenzene in an aqueous acid medium and in the presence of an acid resistant reducing catalyst at an elevated temperature of 130° to 160°C. with hydrogen at an elevated pressure until hydrogen absorption by the reaction ceases, the acid and nitrobenzene being present in at least effective molar quantities; steam distilling from the reaction medium to remove residual nitrobenzene; filtering the catalyst from said reaction medium; adding sufficient water to provide 40 to 90 moles of water per mole of nitrobenzene initially present; maintaining the aqueous reaction medium at a temperature of 200° to 300°C., preferably from 200° to 260°C., for a time sufficient to hydrolyze the hydrogenated product to hydroquinone; cooling the aqueous reaction medium; and extracting the hydroquinone from the cooled aqueous product solution with an organic water-immiscible solvent.

DETAILED DESCRIPTION

The starting material for use in the present invention is nitrobenzene. Two grades of nitrobenzene are commercially available: Nitrobenzene (a technical undistilled product) and oil of mirbane (distilled nitrobenzene). The small amounts of hydrocarbons, both benzene and paraffins, and traces of m-dinitrobenzene, nitrophenol, and water that constitute the impurities in the technical grade do not appreciably affect the process. The oil of mirbane grade has a purity (by freezing point) better than 99.5%.

The acid characteristic of the acid medium may be provided by either phosphoric acid, sulfuric acid, or ammonium bisulfate and either may be of commercial grade. Ammonium bisulfate has the advantage that the ammonium compound that results from the hydrolysis may be regenerated and reused. The acid producing ingredient, phosphoric acid, sulfuric acid, or ammonium bisulfate, is diluted with water to a concentration of ingredient which may range from 10 to 50% by weight of the aqueous medium. The ingredients should be present to the extent of from 1.2 to 10 moles based upon the moles of nitrobenzene.

The nitrobenzene is dispersed in the aqueous medium by agitation. Initially, the nitrobenzene-aqueous medium system in the reactor is a two-phase system; but when the solid catalyst is added, the system becomes a three-phase system. The nitrobenzene can be either the upper liquid phase or the bottom liquid phase, depending upon the concentration of the ingredient employed. For example, concentrations of ammonium bisulfate above 20% have a specific gravity greater than that of nitrobenzene. As the nitrobenzene hydrogenates, the resulting aniline, para-aminophenol, and other compounds dissolve in the aqueous acid solution so that at the completion of hydrogenation only a single liquid phase is present. This single liquid phase is a water white solution that slowly darkens in the presence of air.

The catalytic hydrogenation of nitrobenzene in acidic aqueous mediums is known and is believed to involve the formation of an intermediate product beta-phenylhydroxylamine which is rearranged to form para-aminophenol and aniline. The catalyst, of course, must be an acid resistant hydrogeneration catalyst. Suitable catalysts include the platinum and platinum on carbon that are conventionally used in the conversion of nitrobenzene to p-aminophenol, platinum sulfide on carbon, molybdenum sulfide on carbon, and molybdenum sulfide. While the conventional catalysts such as platinum catalysts are well suited for the preparation of commercially significant quantities of p-aminophenol, they are capable of further hydrogenating the p-aminophenol to alicyclic compounds which are undesirable by-products; particularly where hydrogenation takes place in the presence of a high quantity of platinum catalysts, and the nitrobenzene usually cannot be hydrogenated to completion without overhydrogenation by use of platinum catalysts. Thus, the process should be stopped prior to completion to avoid the formation of undesired alicyclic compounds. Conventional platinum catalysts are easily poisoned and generally are not reusable. A catalyst that is described in my copending application, Ser. No. 447,848, comprises molybdenum sulfide-on-carbon. This catalyst (a) is capable of complete hydrogenation of nitrobenzene without the possibility of overhydrogenation and with the consequential elimination of the usual nitrobenzene recovery step, (b) is not readily poisoned during the preparation of p-aminophenol and (c) is reusable many times before loss of activity. Also a molybdenum sulfide-on-carbon catalyst permits the higher temperatures to be employed during hydrogenation that are preferable, e.g. 155°C. and above, since the rearrangement of the intermediate b-hydroxylamine to p-aminophenol is not only endothermic but is significantly accelerated at the higher temperatures. Acceleration of the rearrangement is important, for if it does not take place, aniline is produced.

The amount of catalyst to be used appears to be a matter of economics. The more of the catalyst that is used, the faster the reaction proceeds. Since the catalyst is expensive, only small quantities are used. It has been found, for example, that 0.050 percent by weight of catalysts based upon the weight of nitrobenzene may be used when the catalyst is 1.0% by weight of platinum on carbon.

The hydrogenation is carried out at temperatures of from 130°C. to 160°C. and at a hydrogen pressure of 50 to 500 pounds per square inch gauge. The completion of the reaction is noted by the decrease in the consumption of hydrogen. Generally, the hydrogenation will require from 3 to 18 hours. The time is dependent upon the type and concentration of catalysts and the temperature and pressures of the reaction.

At the conclusion of the hydrogenation step, from 90 to 98 percent of the nitrobenzene is generally converted to hydrogenation products; which products are a mixture of para-aminophenol, hydroquinone precursors, and aniline. It is desirable in each instance to hydrogenate at those conditions that favor the optimum production of para-aminophenol as this is believed to be the main compound which undergoes hydrolysis to hydroquinone. The aniline seems to remain unchanged by the hydrolysis. The optimum conditions can be readily determined by one skilled in the art when he is using a particular catalyst, temperature, pressure, acid medium, and reaction vessel.

As an example, when it was found that when 91% of the charge of nitrobenzene has been converted to hydrogeneration products, an aliquot product analysis showed a yield based upon the amount of nitrobenzene consumed of 72% para-aminophenol and 15% aniline. The resulting yield after hydrolysis to the product hydroquinone was a 93% yield of hydroquinone based upon the para-aminophenol content and a 67% yield based upon the amount of consumed nitrobenzene. The aniline appeared to remain unchanged. It is believed that the high yield based upon the para-aminophenol is due to some undetermined hydrogenation products which also hydrolyze to hydroquinone. As further illustrations, nitrobenzene was hydrogenated with a conversioon of 94% of the nitrobenzene to amino products which provided a yield of 70% para-aminophenol and 16% aniline based upon the weight of consumed nitrobenzene using 0.03% by weight, based upon the weight of the nitrobenzene, of a catalyst constituted of 5% platinum on a carbon carrier at 250 pounds per square inch gauge of hydrogen for six hours' reaction time at 130°C. and using a mole ratio of one mole of nitrobenzene and one mole of sulfuric acid, while sulfuric acid had been diluted with water to a concentration of 13%. In a like manner, one mole of nitrobenzene was hydrogenated in an aqueous medium containing two moles of phosphoric acid diluted with water to a 40% concentration at a pressure of 150 pounds per square inch gauge of hydrogen and at a temperature of 135°C. For 6 hours in the presence of 0.03% by weight, based upon the weight of nitrobenzene, of the above mentioned platinum-on-carbon catalyst to give a yield of 64% of para-aminophenol and 21% of aniline based upon 100% conversion of the nitrobenzene. Also, a 94% conversion of nitrobenzene was obtained using a salt comprised of 3.5 moles of ammonium bisulfate and 0.35 moles of ammonium sulfate dissolved in a hundred moles of water with 0.11%, based upon the weight of nitrobenzene, of a catalyst comprised of 1% platinum-on-carbon at a temperature of 135°C. for 3 hours and a pressure of 100 pounds per square inch gauge of hydrogen to give a product which was found to provide a yield of 75% of para-aminophenol and 13% of aniline based upon the conversion of the nitrobenzene.

Any nitrobenzene that remains after the hydrogenation is readily removed by steam distillation. The nitrobenzene so recovered can be recycled for use in the next hydrogenation sequence. After the nitrobenzene removal, the aqueous reaction mass is then filtered to remove the catalyst. When molybdenum sulfide on carbon is used as the catalyst, the catalyst can be reused for subsequent reduction reactions. After the catalysts removal, the reaction medium is ready for the hydrolysis reaction.

The composition of the aqueous acid reaction medium becomes important for the hydrolysis. Such composition can be readily determined by analysis. The minimum requirement is that there be at least an effective molar quantity of an acid providing ingredient per mole of nitrobenzene originally present in the reaction.

The hydrolysis can be carried out in one step or it can be carried out in two or more steps. It can be continued sequentially by terminating the reaction, cooling, extracting the hydrolysis product and reheating the hydrolysis mixture without further addition of reactants. A one-step hydrolysis is desirable from the standpoint of ease and efficiency of operation. Usually, an increase in yield can be achieved by a second hydrolysis of the reaction mixture after the product of the first hydrolysis has been extracted. From the standpoint of obtaining high yields in a single hydrolysis step, high concentrations of the acid producing ingredient, in the case of ammonium bisulfate up to the point of saturation of the aqueous solution, is desirable. The point of saturation of the solution when ammonium bisulfate is used is dependent upon the amount of water present and upon the temperature at which the ammonium bisulfate is added to the water.

When ammonium bisulfate is being used, the overall useful range of ammonium bisulfate concentration, as an effective molar quantity, varies between 1.2 and 12 moles of ammonium bisulfate per mole of nitrobenzene originally present with the preferred range being between 3.5 and 5 moles. If less than 1.2 moles of ammonium bisulfate are present, (a) insufficient conversion results; (b) the reaction time is unduly prolonged; and (c) large amount of starting material remains in the aqueous solution. If more than about 12 moles are used, a practical problem arises from the standpoint of handling large quantities of salt.

Water must be present in an amount sufficient to provide for hydrolysis and also to act as solvent for the salts of the hydroquinone precursors, hydroquinone, ammonium bisulfate, the ammonium sulfate, and/or the ammonium phosphate formed during the course of the reaction. As an example, at least 40 moles of water per mole of nitrobenzene originally charged must be present to dissolve sufficient quantities of ammonium bisulfate; and as the concentration of ammonium bisulfate is increased, more water up to about 120 moles, is required. Excess water raises the practical problem of water removal during the ammonium bisulfate regeneration step.

The temperature for the hydrolysis can vary over a wide range of from about 200° to 300°C. If temperatures below about 200°C. are used, an unduly long reaction time is required and the yields are not generally good. As the temperature is increased, the pressure must be correspondingly increased to maintain the reaction medium in the aqueous phase. At temperatures as high as 300°C., a steam pressure of up to about 1250 psig is required to maintain an aqueous phase and there is danger of resin formation if the contact time is too long. No advantage is obtained by increasing or decreasing the pressure to a value other than that which is sufficient to maintain a liquid phase. To avoid the use of considerable pressure, with the corresponding equipment requirements, temperatures in the range of 200° to 260°C. are preferred.

The reaction time or residence time of the reactants during hydrolysis varies with the temperature and to a lesser extent with the mole ratio of the reactants. At minimum temperature, e.g., 200°C., a per pass reaction time of 8 hours is ordinarily required. At 220°C., effective results from the standpoint of yield are obtained using a two-pass hydrolysis reaction and a reaction time of 3 hours per pass. At 220°C., satisfactory results can be obtained in a single pass hydrolysis step if the reaction time is extended to 7 or 8 hours. Depending upon the choice of the reactants, hydrolysis can occur at temperatures above 250°C. in 5 minutes to a half hour. From a practical standpoint, the overall time per pass for hydrolysis can be considered to be from 5 minutes to 8 hours.

Both the hydrogenation and the hydrolysis are to be carried out in a zone which is resistant to any substantial attack by the ammonium bisulfate, ammonium phosphate, sulfuric acid, phosphoric acid, nitrobenzene, hydrogen, hydroquinone, or aminophenol. At very low temperatures within the useful range, an ordinary glass-lined Pfaudler kettle can be used. When higher temperatures and pressurized equipment are required, other construction materials become necessary. At temperatures up to 220° to 230°C., teflon reactors are effective. The higher temperature ranges require the use of more durable equipment such as tantalum-lined reactors.

After the period of hydrolysis, the length of time of which is dependent to some extent on whether a single or multiple pass hydrolysis is used, the reaction mixture is cooled. Cooling is required to prevent resinification of the product in the acidic reaction mixture and to enable the separation of the by-product by organic solvent extraction. Any substantially water-immiscible solvent which will dissolve the product hydroquinone is useful. The preferred solvent is ethyl ether.

In the extraction, the organic solvent phase is then separated from the reaction mixture by decantation and the product is removed from the solvent by distillation or other means. Distillation provides a high purity hydroquinone as a product.

As examples of the acid hyrolysis, analyses have shown that an 82% yield of hydroquinone based upon the analyzed para-aminophenol content are obtained by a two-pass hydrolysis carried on at a temperature of 240°C. for 3 hours for each pass using a mole ratio of one mole of sulfuric acid and 80 moles of water per mole of para-aminophenol. When using phosphoric acid, a yield of 90% of hydroquinone based upon the analyzed para-aminophenol content was obtained by hydrolysis carried out at 240°C. for 2 hours in one pass using a mole ratio of 2 moles of phosphoric acid and 60 moles of water per mole of para-aminophenol. A two-pass hydrolysis using ammonium bisulfate at a temperature of 240°C. for 3 hours for each pass with a mole ratio of 2 moles of ammonium bisulfate and 60 moles of water per mole of the analyzed para-aminophenol content gave a yield of 82% of hydroquinone based upon the para-aminophenol.

The by-product aniline is not hydrolyzed under the conditions used to hydrolyze the para-aminophenol to hydroquinone. The aniline can be recovered, after the hydroquinone has been removed from the aqueous reaction medium, by neutralizing the aqueous reaction medium with ammonia and steam distilling the aniline from the reaction medium.

After removal of the hydroquinone and the aniline, the resulting aqueous effluent reaction mixture can be reheated to the hydrolysis temperature for a second or even a third hydrolysis step. The second and subsequent hydrolysis steps are carried out as before; i.e., by heating the reaction mixture to the appropriate temperature of hydrolysis for the desired period of time, cooling and removing the hydroquinone product by solvent extraction.

Ammonium bisulfate is regenerated for reuse in the process by removing the residual water from the remaining reaction mixture and heating the molten salt, primarily mixed ammonium sulfate, and ammonium bisulfate at atmospheric pressure at a temperature between 310° and 450°C. An unduly long time is required to effect decomposition at temperatures below 310°C., and no practical advantage is seen in using temperatures higher than 450°C.; especially as the bisulfate tends to decompose at temperatures higher than 450°C. At 330°C., 75 to 95 percent of the ammonium sulfate is converted within a few minutes to ammonium bisulfate. Slightly higher conversions are obtained at higher temperatures, but this advantage of higher conversion is offset by the increased equipment cost required. During the decomposition of the ammonium sulfate, residual organic materials may be pyrolyzed to black granules resembling activated charcoal but such granules can be removed by dissolving the product in water and filtering it. The ammonia formed during the decomposition can be recovered and used in other chemical processes. The clear, filtered salt solution, the salt portion which 75 to 95 percent is ammonium bisulfate, may be adjusted to the desired concentration and be recycled to the reaction mixture for hydrolysis of additional hydrogenation of nitrobenzene or hydrolysis of the hydrogeneration product.

Without further elaboration, it is believed that one skilled in the art can, be following the preceding description, utilize the present invention to its fullest extent. The following specific embodiments are, therefore, to be construed as merely illustrative, and not limitative of the disclosure.

EXAMPLE I

To a 30-gallon glass-lined Pfaudler autoclave was charged nitrobenzene (8.30 lbs.), $NH_4HSO_4$ (27.00 lbs.), $(NH_4)_2SO_4$ (3.14 lbs.), $H_2O$ (121.50 lbs.), 1% Pt/C catalyst (4.00 g.), and 150 drops of Igepal 60 emulsifying agent. After a nitrogen purge the autoclave was heated to 135°C. under 10 psi of $H_2$. The hydrogen pressure was purposely kept low during heat-up so that no hydrogenation would take place until reaction temperature was reached because hydrogenation at a lower than reaction temperature has been found to favor aniline formation. Then the agitator speed was adjusted to 170 rpm and the hydrogen pressure raised to 120 psi of $H_2$. The hydrogen absorption rate was maintained at a pressure of 170 to 140 psi/hr. for 2½ hrs. and 12 psi/hr. for the last ½ hour. The hydrogen pressure was purposely adjusted to maintain an absorption rate that would extend the hydrogenation to a period of 3 hours.

At the end of the hydrogenation reaction period, any unreacted nitrobenzene was steam distilled from the aqueous reaction medium in the autoclave. Nitrobenzene (350 g.) was collected; this indicated a conversion of 91% of the nitrobenzene to hydrogenated products. Water equal to the water distilled over with the nitrobenzene was returned to the autoclave to maintain the original concentration of water.

The hydrogenate was filtered of catalyst through double layers of paper on a Nutsche type filter. A sample of the filtrate was taken for analysis; and it showed that based upon the amount of consumed or converted nitrobenzene, there was a yield of 16 mole % aniline and 75 mole % para-aminophenol.

The filtrate was returned to an acid resistant autoclave (tantalum lined). After a nitrogen purge, the autoclave was heated to 250°C. for ½ hour and maintained at this temperature of 1½ hours. After cooling to room temperature, 118.5 g. of solids were filtered from the hydrolyzate. The filtrate was extracted with ethyl ether. The ethyl ether was neutralized with sodium bicarbonate, filtered and distilled. The residue of crude hydroquinone was 2190 g. (81.8%). Distillation of the crude product gave 1949 g. (72.7%) based on nitrobenzene consumed of hydroquinone, b.p. 192 to 194°C./40 mm., and 162 g. (6.1%) of a non-distillable residue.

The aqueous reaction medium that remained from the process as illustrated above was regenerated to provide bisulfate for recycling. To this end, the water evaporated to provide a dry salt that was about an equal mixture of ammonium bisulfate and ammonium sulfate. This dry salt was heated in an oil bath. The salt was stirred easily after it reached the temperature of 146°C., the melting point of ammonium bisulfate. As heating was continued to a temperature of 312°C., ammonium evolved. The melt was held at this temperature of 312°C. for 12 minutes. After this time, analysis revealed the ammonium bisulfate content to be 95%. During the heating of the melt, the organic material in the melt changed to fine carbonaceous particles. Dissolving the thermally treated salt mixture in water and filtering it produced a clear filtrate solution. Evaporation of the water from the filtrate yield light yellow ammonium bisulfate crystals. The ammonium bisulfate so produced was suitable for recycling for use in the hydrogenation or hydrolyzing step, to produce more amino product to hydroquinone.

The following is a tabulation wherein the mol ratios and yields in the hydrogenation step are by weight based upon the weight of nitrobenzene originally charged. The yield based on para-aminolphenol is based upon the analyzed result. The yield and mol ratios in the hydrolysis reaction are based upon the amount of nitrobenzene actually consumed in the hydrogenation reaction. The acid ingredient used was ammonium bisulfate.

| HYDROGENATION | |
| --- | --- |
| Acid Mol Ratio | 3.5 |
| Acid Concentration % | 17.7 |
| Catalyst Type | 1% Pt/c |
| Catalyst Concentration % | 0.107 |
| Time, hours | 3.0 |
| Temp., °C. | 135 |
| Pressure, psig Hydrogen | 120 |
| Para-aminophenol Yield % | 75 |
| Aniline Yield % | 16 |
| Nitrobenzene Consumed, % of Charge | 91 |
| HYDROLYSIS | |
| Acid Mol Ratio | 3.8 |
| Water Mol Ratio | 114 |
| No. of Passes | 2 |
| Time/Pass, Hours | 1½ |
| Temp., °C. | 250 |
| Hydroquinone Yield based on Para-aminophenol % | 92 |
| Hydroquinone Yield based on Nitrobenzene % | 67 |
| Aniline Yield % | 16 |

EXAMPLE II

The procedure of Example II was repeated except that sulfuric acid was used to provide the acid characteristic to the aqueous medium. The resulting products were hydroquinone, aniline and ammonium bisulfate. The results are tabulated below on the same basis as described for Example I.

| HYDROGENATION | |
| --- | --- |
| Acid Mol Ratio | 1.0 |
| Acid Concentration | 13% |
| Catalyst Type | 5% P/c |
| Catalyst Concentration % | .015 |
| Time, hours | 8 |
| Temp., °C. | 130 |
| Pressure, psig Hydrogen | 250 |
| Para-aminophenol Yield % | 68 |
| Aniline Yield % | 14 |
| Nitrobenzene Consumed, % of Charge | 65 |

The reaction medium was analyzed and the acid and water ratios adjusted.

| HYDROLYSIS | |
| --- | --- |
| Acid Mol Ratio | 1.0 |
| Water Mol Ratio | 80.0 |
| No. of Passes | 2 |
| Time/Pass, Hours | 3 |
| Temp., °C. | 240 |
| Hydroquinone Yields based on Para-aminophenol % | 91.2 |
| Hydroquinone Yields based on Nitrobenzene % | 62 |
| Aniline Yield % | 14 |

The by-product ammonium sulfate is convertable to ammonium bisulfate as described in Example I.

EXAMPLE III

The procedure of Example I was repeated except that phosphoric acid was used to provide the acid characteristic to the acid medium. The resulting products were hydroquinone, aniline and ammonium phosphate compounds. Ammonium phosphate compounds cannot be reused as can the ammonium sulfate compounds but can be used for other purposes as, for example, for fertilizers. The results are tabulated below on the same basis as described for Example I.

| HYDROGENATION | |
| --- | --- |
| Acid Mol Ratio | 2.0 |
| Acid Concentration | 23 |
| Catalyst Type | 5% Pt/c |

-continued

| | |
|---|---|
| Catalyst Concentration % | 0.021 |
| Time, hours | 8 |
| Temp., °C. | 135 |
| Pressure, psig Hydrogen | 115-150 |
| Para-aminophenol Yield % | 55 |
| Aniline Yield % | 16 |
| Nitrobenzene Consumed, % of Charge | 96.7 |

The reaction medium was analyzed and the acid and water ratios adjusted.

| HYDROLYSIS | |
|---|---|
| Acid Mol Ratio | 4 |
| Water Mol Ratio | 120 |
| No. of Passes | 2 |
| Time/Pass, Hours | 3 |
| Temp., °C. | 240 |
| Hydroquinone Yield based on Para-aminophenol % | 118 |
| Hydroquinone Yield based on Nitrobenzene % | 65.1 |
| Aniline Yield % | 16 |

What is claimed is:
1. A process for producing hydroquinone comprising:
   a. hydrogenating nitrobenzene in an aqueous acid medium and in the presence of an acid resistant reducing catalyst selected from the group consisting of platinum, platinum on carbon, platinum sulfide on carbon, molybdenum sulfide on carbon and molybdenum sulfide at an elevated temperature at 130° to 160°C at an elevated pressure until hydrogen absorption by the nitrobenzene ceases; the ingredient for imparting acid characteristics to the medium being present in at least an effective molar quantity with respect to the nitrobenzene and being selected from the group consisting of sulfuric acid, phosphoric acid and ammonium bisulfate;
   b. steam distilling residual nitrobenzene from the reaction medium;
   c. filtering the catalyst from the reaction medium;
   d. adding sufficient water to provide 40 to about 120 moles of water per mole of nitrobenzene initially present;
   e. maintaining the aqueous reaction medium at a temperature of from 200 to 300°C from a time sufficient to hydrolyze the hydrogenated product to hydroquinone,
   f. cooling the aqueous reaction medium, and
   g. extracting the hydroquinone from said cooled aqueous reaction medium with an organic water-immiscible solvent.

2. The process of claim 1 wherein said ingredient is sulfuric acid and it is present in at least a molar quantity equal to the molar quantity of nitrobenzene.

3. The process of claim 1 wherein said ingredient is phosphoric acid and it is present in the ratio of at least 4 moles per mole of nitrobenzene.

4. The process of claim 1 wherein said ingredient is ammonium bisulfate and it is present in the mol ratio of at least 3.5 moles per mole of nitrobenzene.

5. The process of claim 1 wherein the aqueous reaction medium from which the hydroquinone has been extracted is then heated to a temperature of from 200° to 300°C. to hydrolyze additional hydrogenated product to hydroquinone.

6. The process of claim 4 wherein the aqueous reaction medium from which the hydroquinone has been extracted is subjected to evaporation to obtain a residue consisting essentially of ammonium sulfate and the residue is heated to an elevated temperature of from 310° to 450°C. to convert the ammonium sulfate content to ammonium bisulfate for use as another quantity of said ingredient.

7. The process of claim 1 wherein the temperature of the reaction medium after the extraction of hydroquinone is maintained at between 220° and 260°C. for the hydrolysis of additional of hydrogenated product to hydroquinone.

* * * * *